United States Patent
Bailey et al.

(10) Patent No.: US 9,408,316 B2
(45) Date of Patent: Aug. 2, 2016

(54) SYSTEMS, ARTICLES AND METHODS FOR STRAIN MITIGATION IN WEARABLE ELECTRONIC DEVICES

(71) Applicant: Thalmic Labs Inc., Kitchener (CA)

(72) Inventors: Matthew Bailey, Kitchener (CA);
Stephen E. Orzel, Hamilton (CA);
Graham T. Hills, Hamilton (CA)

(73) Assignee: THALMIC LABS INC., Kitchener (CA)

( * ) Notice: Subject to any disclaimer, the term of this patent is extended or adjusted under 35 U.S.C. 154(b) by 196 days.

(21) Appl. No.: 14/335,688

(22) Filed: Jul. 18, 2014

(65) Prior Publication Data

US 2015/0025355 A1    Jan. 22, 2015

Related U.S. Application Data

(60) Provisional application No. 61/857,105, filed on Jul. 22, 2013.

(51) Int. Cl.
*H05K 5/02*       (2006.01)
*H05K 7/02*       (2006.01)
(Continued)

(52) U.S. Cl.
CPC ............ *H05K 5/0217* (2013.01); *A61B 5/0492* (2013.01); *A61B 5/681* (2013.01); *A61B 5/6831* (2013.01); *H05K 7/026* (2013.01)

(58) Field of Classification Search
CPC ........ A61B 5/02; A61B 5/681; A61B 5/0492; A61B 5/6831; H05K 5/0217; H05K 7/026
See application file for complete search history.

(56) References Cited

U.S. PATENT DOCUMENTS 5,482,051 A    1/1996 Reddy
5,683,404 A    11/1997 Johnson
(Continued)

FOREIGN PATENT DOCUMENTS

EP     0301790 A2    2/1989
WO     2011070554 A2    6/2011

OTHER PUBLICATIONS

Morris et al., "Emerging Input Technologies for Always-Available Mobile Interaction," Foundations and Trends in Human-Computer Interaction, vol. 4, No. 4 (2010), pp. 245-316.
(Continued)

*Primary Examiner* — Nabil Syed
(74) *Attorney, Agent, or Firm* — Seed IP Law Group PLLC

(57) ABSTRACT

Wearable electronic devices that provide adaptive physical coupling between electrically coupled components are described. Adaptive physical coupling advantageously accommodates different user sizes, forms, and movements and enhances the overall ergonomics of a wearable electronic device. Adaptive physical coupling also introduces stresses and strains on electrical pathways between the electrically coupled components. Accordingly, the wearable electronic devices include strain mitigation systems that mitigate physical strains on the electrical pathways between electrically coupled components. An exemplary strain mitigation system includes a guide structure that is pivotally coupled to a first substantially rigid structure of the wearable electronic device and slideably coupled to a second substantially rigid structure of the wearable electronic device. The guide structure provides a surface/channel over/through which electrical pathways extend between electrically coupled components.

25 Claims, 5 Drawing Sheets

(51) Int. Cl.
*A61B 5/00* (2006.01)
*A61B 5/0492* (2006.01)

(56) References Cited

U.S. PATENT DOCUMENTS

| | | | |
|---|---|---|---|
| 6,032,530 | A | 3/2000 | Hock |
| 6,244,873 | B1 | 6/2001 | Hill |
| 6,487,906 | B1 | 12/2002 | Hock |
| 6,720,984 | B1 | 4/2004 | Jorgensen |
| 7,333,090 | B2 | 2/2008 | Tanaka |
| 7,596,393 | B2 | 9/2009 | Jung |
| 8,170,656 | B2 | 5/2012 | Tan |
| 8,447,704 | B2 | 5/2013 | Tan |
| 2002/0032386 | A1 | 3/2002 | Sackner |
| 2003/0144586 | A1* | 7/2003 | Tsubata ............ A61B 5/022 600/407 |
| 2004/0210165 | A1 | 10/2004 | Marmaropoulos |
| 2010/0280628 | A1 | 11/2010 | Sankai |
| 2010/0293115 | A1 | 11/2010 | Momen |
| 2012/0203076 | A1* | 8/2012 | Fatta ............ A61B 5/681 600/300 |
| 2013/0027341 | A1 | 1/2013 | Mastandrea |
| 2014/0236031 | A1* | 8/2014 | Banet ............ A61B 5/6831 600/513 |
| 2014/0364703 | A1* | 12/2014 | Kim ............ A61B 5/0492 600/301 |

OTHER PUBLICATIONS

Costanza et al., "EMG as a Subtle Input Interface for Mobile Computing," MobileHCI 2004, LNCS 3160, edited by S. Brewster and M. Dunlop, pp. 426-430, 2004, Springer-Verlag Berlin Heidelberg.

Costanza et al., "Toward Subtle Intimate Interfaces for Mobile Devices Using an EMG Controller," CHI 2005, Proceedings of the SIGCHI Conference on Human Factors in Computing Systems, p. 481-489.

Rekimoto, Jun, "GestureWrist and GesturePad: Unobtrusive Wearable Interaction Devices," ISWC '01 Proceedings of the 5th IEEE International Symposium on Wearable Computers, p. 21-27.

Zhang et al., "A Framework for Hand Gesture Recognition Based on Accelerometer and EMG Sensors," IEEE Transactions on Systems, Man, and Cybernetics—Part A: Systems and Humans, vol. 41, No. 6, Nov. 2011, 13 pages.

Ghasemzadeh et al., "A Body Sensor Network with Electromyogram and Inertial Sensors: Multimodal Interpretation of Muscular Activities," IEEE Transactions on Information Technology in Biomedicine, vol. 14, No. 2, Mar. 2010, p. 198-206.

Xiong et al., "A Novel HCI based on EMG and IMU," Proceedings of the 2011 IEEE International Conference on Robotics and Biometrics, Dec. 7-11, 2011, Phuket, Thailand, p. 2653-2657.

Naik et al., "Real-Time Hand Gesture Identification for Human Computer Interaction Based on ICA of Surface Electromyogram," IADIS International Conference Interfaces and Human Computer Interaction 2007, p. 83-90.

Saponas et al., "Making Muscle-Computer Interfaces More Practical," CHI 2010, Apr. 10-15, 2010, Atlanta, Georgia, USA, 4 pages.

Picard et al., "Affective Wearables," Proceedings of the IEEE 1st International Symposium on Wearable Computers, ISWC, Cambridge, MA USA, Oct. 13-14, pp. 91-97 (1997).

International Search Report, mailed May 16, 2014, for PCT/US2014/017799, 11 pages.

International Search Report, mailed Aug. 21, 2014, for PCT/US2014/037863, 12 pages.

* cited by examiner

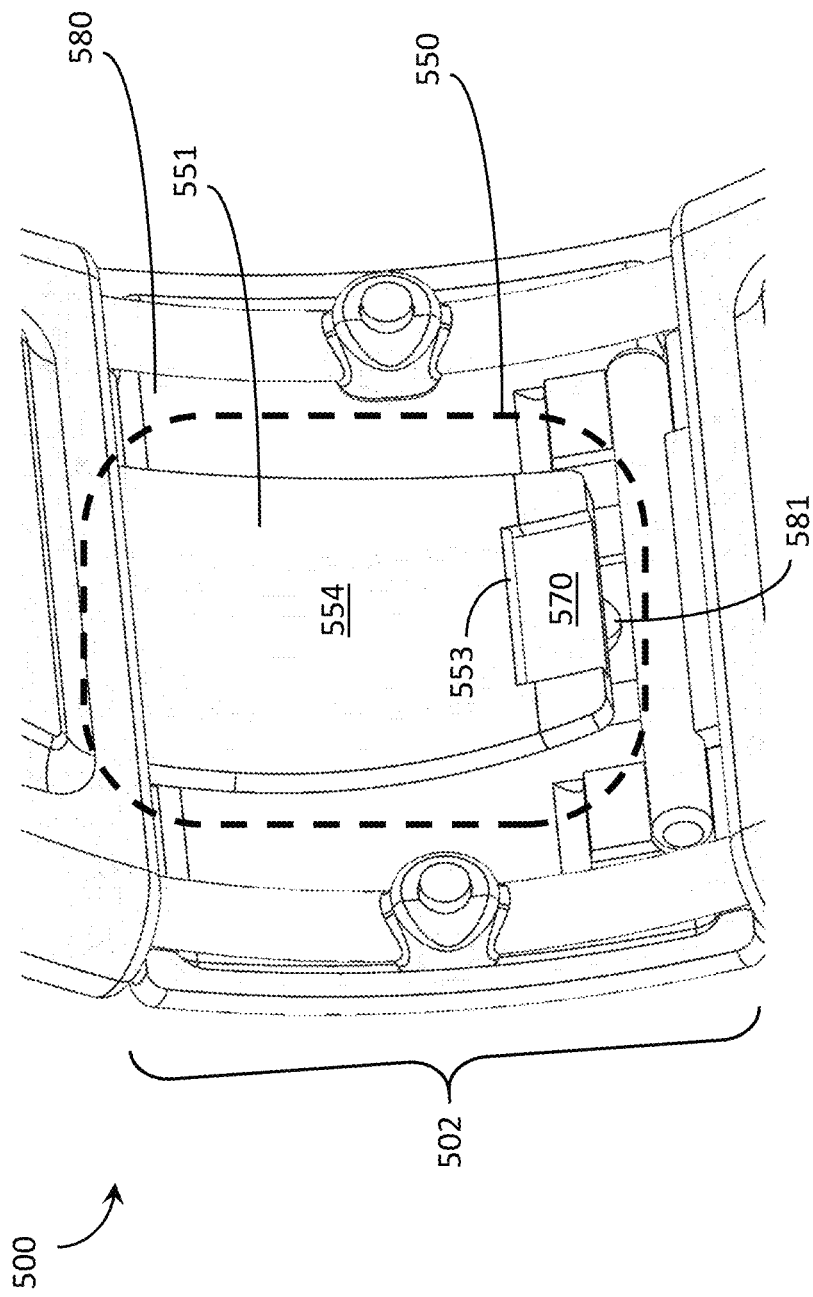

SYSTEMS, ARTICLES AND METHODS FOR STRAIN MITIGATION IN WEARABLE ELECTRONIC DEVICES

BACKGROUND

1. Technical Field

The present systems, articles and methods generally relate to wearable electronic devices and particularly relate to systems, articles and methods that mitigate physical strain on wiring components in wearable electronic devices.

2. Description of the Related Art

Wearable Electronic Devices

Electronic devices are commonplace throughout most of the world today. Advancements in integrated circuit technology have enabled the development of electronic devices that are sufficiently small and lightweight to be carried by the user. Such "portable" electronic devices may include on-board power supplies (such as batteries or other power storage systems) and may be designed to operate without any wire-connections to other electronic systems; however, a small and lightweight electronic device may still be considered portable even if it includes a wire-connection to another electronic system. For example, a microphone may be considered a portable electronic device whether it is operated wirelessly or through a wire-connection.

The convenience afforded by the portability of electronic devices has fostered a huge industry. Smartphones, audio players, laptop and tablet computers, and ebook readers are all examples of portable electronic devices. However, the convenience of being able to carry an electronic device has also introduced the inconvenience of having one's hand(s) encumbered by the device itself. This problem is addressed by making an electronic device not only portable, but wearable.

A wearable electronic device is any portable electronic device that a user can carry without physically grasping, clutching, or otherwise holding onto the device with their hands. For example, a wearable electronic device may be attached or coupled to the user by a strap or straps, a band or bands, a clip or clips, an adhesive, pin and clasp, an article of clothing, tension or elastic support, an interference fit, an ergonomic form, etc. Examples of wearable electronic devices include digital wristwatches, electronic armbands, electronic rings, electronic ankle-bracelets or "anklets," head-mounted electronic display units, hearing aids, and so on.

A wearable electronic device is subjected to the movements of the user. For example, a wearable electronic device may be pushed, pulled, stretched, compressed, twisted, shocked, shaken, and/or generally exposed to stresses and strains that would not typically be encountered by non-wearable electronic devices. Wiring that connects (i.e., electrically couples) between components in a wearable electronic device is particularly sensitive to these stresses and strains. The risk of detachment of such wiring significantly limits the practicality, adoptability, and ultimate viability of any wearable electronic device. Accordingly, there is a need in the art for wearable electronic devices that incorporate systems, articles, and methods to mitigate physical strain on internal wiring.

Human-Electronics Interfaces

A wearable electronic device may provide direct functionality for a user (such as audio playback, data display, computing functions, etc.) or it may provide electronics to interact with, receive information from, or control another electronic device. For example, a wearable electronic device may include sensors that detect inputs from a user and transmit signals to another electronic device based on those inputs. Sensor-types and input-types may each take on a variety of forms, including but not limited to: tactile sensors (e.g., buttons, switches, touchpads, or keys) providing manual control, acoustic sensors providing voice-control, electromyography sensors providing gesture control, and/or accelerometers providing gesture control.

A human-computer interface ("HCI") is an example of a human-electronics interface. The present systems, articles, and methods may be applied to wearable human-computer interfaces, but may also be applied to any other form of wearable human-electronics interface.

BRIEF SUMMARY

A wearable electronic device may be summarized as including a first pod structure that includes electrical circuitry; a second pod structure that includes electrical circuitry; a first adaptive coupler that provides adaptive physical coupling between the first pod structure and the second pod structure; a first set of electrically conductive pathways to in use provide electrical coupling between the electrical circuitry of the first pod structure and the electrical circuitry of the second pod structure; and a first strain mitigation system to in use mitigate strain on the first set of electrically conductive pathways, the first strain mitigation system comprising a first guide structure that is physically coupled to the first pod structure and projects at least partially over the electrical circuitry of the second pod structure, wherein a respective first portion of each electrically conductive pathway in the first set of electrically conductive pathways extends across a length of the first guide structure. The first adaptive coupler may include an elastic material that is physically coupled to both the first pod structure and the second pod structure to, in use, provide elastic physical coupling between the first pod structure and the second pod structure. The first strain mitigation system may further include at least one pivot structure, and the first guide structure may be pivotally coupled to the first pod structure through the at least one pivot structure.

The first set of electrically conductive pathways may include a first flexible printed circuit board. The first guide structure may include a first surface, an edge, and a second surface opposite the first surface, and a first portion of the first flexible printed circuit board may extend across a length of the first surface of the first guide structure, a second portion of the first flexible printed circuit board may bend around the edge of the first guide structure, and a third portion of the first flexible printed circuit board may extend across at least a portion of a length of the second surface of the first guide structure. The first guide structure may include a recessed channel that extends across a length of the first guide structure, and the first flexible printed circuit board may extend across a length of the first guide structure within the recessed channel in the first guide structure.

The first strain mitigation system may be slideably coupled to the second pod structure. One of the first strain mitigation system and the second pod structure may include a receiving channel and the other of the first strain mitigation system and the second pod structure may include a protrusion that protrudes into the receiving channel, and slideable coupling between the first strain mitigation system and the second pod structure may be through the protrusion and the receiving channel.

The first pod structure and the second pod structure may each be formed of substantially rigid material. The second pod structure may include a housing having an inner volume, and the first guide structure may project at least partially into the inner volume of the housing of the second pod structure.

The second pod structure may be positioned adjacent the first pod structure, and the wearable electronic device ma further include a third pod structure that includes electrical circuitry, the third pod structure positioned adjacent the second pod structure; an adaptive physical coupling between the second pod structure and the third pod structure; a second set of electrically conductive pathways to in use provide electrical coupling between the electrical circuitry of the second pod structure and the electrical circuitry of the third pod structure; and a second strain mitigation system to in use mitigate strain on the second set of electrically conductive pathways, the second strain mitigation system comprising a second guide structure that is physically coupled to the second pod structure and projects at least partially over the electrical circuitry of the third pod structure, wherein a respective first portion of each electrically conductive pathway in the second set of electrically conductive pathways extends across a length of the second guide structure. The adaptive physical coupling between the second pod structure and the third pod structure may be through the first adaptive coupler. The wearable electronic device may further include a second adaptive coupler that provides the adaptive physical coupling between the second pod structure and the third pod structure. The wearable electronic device may further include an adaptive physical coupling between the third pod structure and the first pod structure. The wearable electronic device may further include at least one additional pod structure that includes electrical circuitry, each additional pod structure positioned adjacent at least one other pod structure; a respective adaptive physical coupling between each additional pod structure and an adjacent at least one other pod structure; a respective additional set of electrically conductive pathways corresponding to each additional pod structure, wherein each additional set of electrically conductive pathways in use provides electrical coupling between the electrical circuitry of a corresponding additional pod structure and the electrical circuitry of the adjacent at least one other pod structure; and a respective additional strain mitigation system corresponding to each additional set of electrically conductive pathways, each additional strain mitigation system to in use mitigate strain on a corresponding additional set of electrically conductive pathways, wherein each additional strain mitigation system comprises a respective corresponding guide structure that is physically coupled to the adjacent at least one other pod structure and projects at least partially over the electrical circuitry of the corresponding additional pod structure, and wherein a respective first portion of each electrically conductive pathway in the corresponding additional set of electrically conductive pathways extends across a length of the respective corresponding guide structure. The first pod structure, the second pod structure, the third pod structure, and the at least one additional pod structure may be collectively arranged in an annular configuration with each respective pod structure positioned adjacent two other pod structures.

At least one of the first pod structure and the second pod structure may include an electromyography sensor.

A wearable electronic device may be summarized as including a set of pod structures arranged in an annular configuration with each pod structure in the set of pod structures positioned adjacent two other pod structures in the set of pod structures, wherein each pod structure includes respective electrical circuitry; an adaptive coupler that physically couples each pod structure in the set of pod structures to two adjacent pod structures in the set of pod structures, wherein the adaptive coupler physically binds the set of pod structures in the annular configuration; a plurality of electrically conductive pathway sets, wherein each respective pair of adjacent pod structures in the set of pod structures is electrically coupled together by a respective electrically conductive pathway set in the plurality of electrically conductive pathway sets; and a set of strain mitigation systems, each to in use mitigate strain on a respective electrically conductive pathway set in the plurality of electrically conductive pathway sets, wherein each strain mitigation system includes a respective guide structure that is physically coupled to a respective pod structure in the set of pod structures and that projects at least partially over or within an adjacent pod structure in the set of pod structures, and wherein each electrically conductive pathway set in the plurality of electrically conductive pathway sets extends across a length of the guide structure of a respective strain mitigation system in the set of strain mitigation systems. The adaptive coupler may include elastic material. The adaptive coupler may include at least two disconnected pieces of elastic material, or the adaptive coupler may consist of a single piece of elastic material.

Each strain mitigation system in the set of strain mitigation systems may include at least one respective pivot structure, and the respective guide structure of each strain mitigation system in the set of strain mitigation systems may be pivotally coupled to a respective pod structure through the at least one respective pivot structure.

Each electrically conductive pathway set in the plurality of electrically conductive pathway sets may include a respective flexible printed circuit board.

Each respective guide structure may include a respective first surface, a respective edge, and a respective second surface opposite the respective first surface, and for each flexible printed circuit board: a first portion of the flexible printed circuit board may extend across a length of the first surface of a corresponding guide structure, a second portion of the flexible printed circuit board may bend around the edge of the corresponding guide structure, and a third portion of the flexible printed circuit board may extend across at least a portion of a length of the second surface of the corresponding guide structure. The first surface of each guide structure may include a respective recessed channel, and for each flexible printed circuit board: the first portion of the flexible printed circuit board may extend across the length of the first surface of the corresponding guide structure within the recessed channel in the first surface of the corresponding guide structure.

Each strain mitigation system may includes a respective slideable coupling between the respective guide structure and the adjacent pod structure in the set of pod structures over or within which the respective guide structure projects.

Each pod structure in the set of pod structures may be formed of substantially rigid material. Each pod structure in the set of pod structures may include a respective housing having a respective inner volume, and each respective guide structure may project at least partially into the inner volume of the respective housing of a respective adjacent pod structure in the set of pod structures.

At least one pod structure in the set of pod structures may include an electromyography sensor.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 5 is a perspective view of a portion of an exemplary wearable electronic device including a pod structure and a guide structure slideably coupled to the pod structure in accordance with the present systems, articles and methods.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electronic devices, and in particular portable electronic devices such as wearable electronic devices, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

The various embodiments described herein provide systems, articles, and methods for strain mitigation in wearable electronic devices. In particular, improved wearable electronic device designs incorporate the present systems, articles, and methods to mitigate physical strain on internal wiring components.

Figure 1:
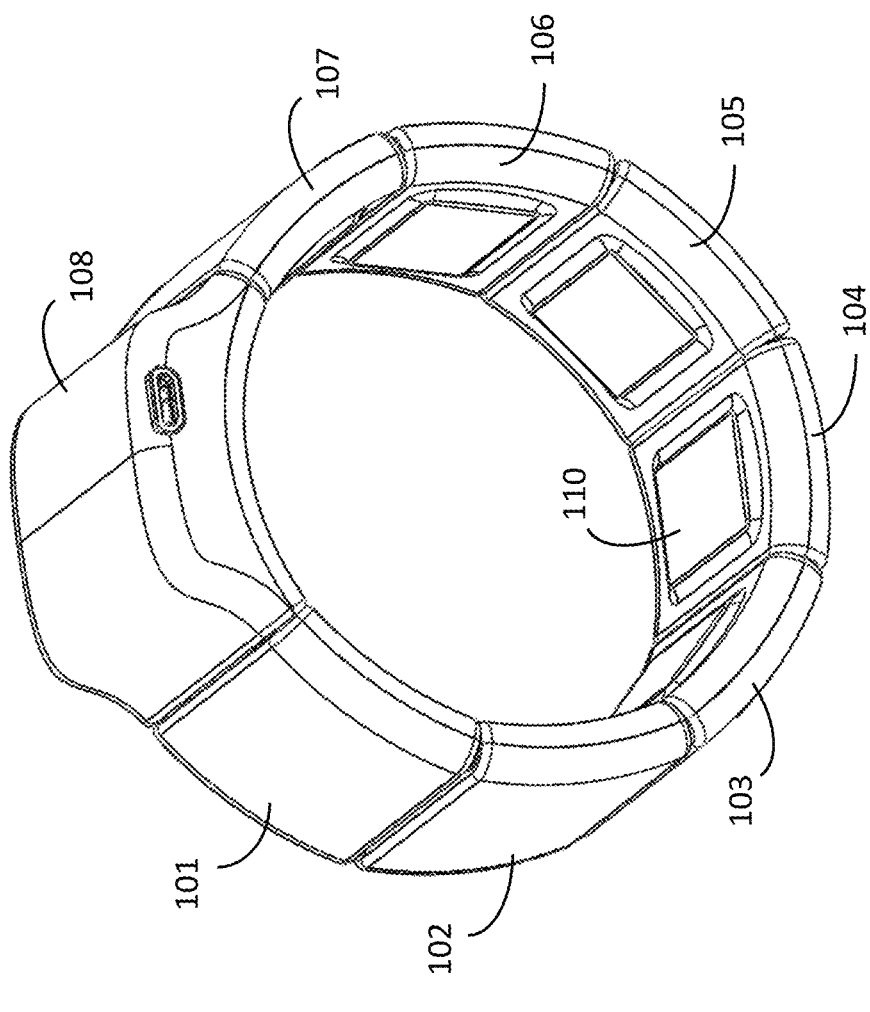
FIG. 1 is a perspective view of an exemplary wearable electronic device that includes built-in systems, articles, and methods for mitigating physical strain on internal wiring in accordance with the present systems, articles and methods.

FIG. 1 is a perspective view of an exemplary wearable electronic device 100 that includes built-in systems, articles, and methods that in use mitigate physical strain on internal wiring components in accordance with the present systems, articles and methods. Exemplary device 100 is an armband designed to be worn on the wrist, forearm, or upper arm of a user, though a person of skill in the art will appreciate that the teachings described herein may readily be applied in wearable electronic devices designed to be worn elsewhere on the body of the user (e.g., on the leg, ankle, finger, neck, or torso). Device 100 includes a set of eight segments or "pod structures" 101, 102, 103, 104, 105, 106, 107, and 108 arranged in an annular configuration such that each pod structure in the set of eight pod structures is positioned adjacent (e.g., in between) two other pod structures in the set of eight pod structures. For example, pod structure 101 is positioned adjacent pod structures 102 and 108, pod structure 102 is positioned adjacent pod structures 101 and 103, pod structure 103 is positioned adjacent pod structures 102 and 104, and so on. Each pod structure in the set of eight pod structures is physically coupled to the two adjacent pod structures by an adaptive coupler (not shown). For example, pod structure 101 is physically coupled to pod structure 108 by an adaptive coupler and to pod structure 102 by an adaptive coupler. The term "adaptive coupler" is used throughout this specification and the appended claims to denote a system, article or device that provides flexible, adjustable, modifiable, conformable, or otherwise "adaptive" physical coupling. Adaptive coupling is physical coupling between two objects that permits limited motion of the two objects relative to one another. An example of an adaptive coupler is an elastic material such as an elastic band. Thus, each pod structure in the set of eight pod structures may be physically coupled to the two adjacent pod structures by at least one elastic band. The set of eight pod structures may be physically bound in the annular configuration by a single elastic band that couples over or through all pod structures or by multiple disconnected elastic bands that couple between adjacent pairs of pod structures or between groups of adjacent pairs of pod structures. Device 100 is depicted in FIG. 1 with the adaptive coupler completely retracted and contained within the eight pod structures 101, 102, 103, 104, 105, 106, 107, and 108 (and therefore the adaptive coupler is not visible in FIG. 1).

As device 100 is a wearable electronic device, any or all of pod structures 101, 102, 103, 104, 105, 106, 107, and/or 108 may include electrical circuitry (not shown in FIG. 1). Exemplary device 100 depicted in FIG. 1 is a wearable electromyography device for which each of pod structures 101, 102, 103, 104, 105, 106, 107, and 108 includes a respective electromyography sensor 110 (only one called out in FIG. 1 to reduce clutter) and associated electrical circuitry (not shown in FIG. 1). Further details of exemplary electromyography device 100 are described in U.S. Provisional Patent Application Ser. No. 61/752,226 (now U.S. Non-Provisional patent application Ser. No. 14/155,107), U.S. Provisional Patent Application Ser. No. 61/768,322 (now U.S. Non-Provisional patent application Ser. No. 14/186,889), and U.S. Provisional Patent Application Ser. No. 61/771,500 (now U.S. Non-Provisional patent application Ser. No. 14/194,252), each of which is incorporated herein by reference in its entirety. Those of skill in the art will appreciate, however, that a wearable electronic device having electromyography functionality is used only as an example in the present systems, articles, and methods and that the systems, articles and methods for mitigating physical strain on internal wiring components in wearable electronic devices described herein are in no way limited to wearable electronic devices that employ electromyography sensors unless explicitly recited in a respective claim to such.

Throughout this specification and the appended claims, the term "pod structure" is used to refer to an individual segment, pod, section, component, etc. of a wearable electronic device, where the individual segment, pod, section, component, etc. includes or carries electrical circuitry. For the purposes of the present systems, articles, and methods, an "individual segment, pod, section, component, etc." of a wearable electronic device is characterized by its ability to be moved or displaced relative to another segment, pod, section, component, etc. of the wearable electronic device. For example, segments 101 and 102 of device 100 are respective "pod structures" of device 100 because segments 101 and 102 can each be moved or displaced relative to one another (within the constraints imposed by the adaptive coupler) and segments 101 and 102 each include or carry electrical circuitry. The need for pod structures 101 and 102 to be movable/displaceable relative to one another specifically arises because device 100 is a wearable electronic device that must accommodate the movements of a user.

In a wearable electronic device that employs multiple pod structures (such as device 100 from FIG. 1), each pod structure may also be characterized by a need to be electrically connected or electrically coupled to and/or through at least one other pod structure within the wearable electronic device. Thus, device 100 also includes a plurality of electrically conductive pathway sets (not shown in FIG. 1), where each respective pair of adjacent pod structures 101, 102, 103, 104, 105, 106, 107, and 108 is electrically coupled together by a respective electrically conductive pathway set. As a consequence of the requirement for adjacent pairs of pod structures 101, 102, 103, 104, 105, 106, 107, and 108 to be both electrically coupled together and movable/displaceable relative to one another, the electrically conductive pathway sets that provide electrical coupling between and/or through adjacent pairs of pod structures 101, 102, 103, 104, 105, 106, 107, and 108 are exposed to stresses and strains that can ultimately cause at least some electrically conductive pathway sets to break and/or to become detached. The various embodiments described herein provide systems, articles, and methods that mitigate stresses and strains to which wiring components in wearable electronic devices are exposed and thereby enhance the robustness, longevity, practicality, and overall viability of wearable electronic devices.

Many of the features and details described above (e.g., adaptive coupler(s), electrically conductive pathway sets, electrical circuitry, etc.) are not shown in FIG. 1 because FIG. 1 depicts pod structures 101, 102, 103, 104, 105, 106, 107, and 108 with such components contained within the respective inner volumes of closed and optically opaque housings. The features described but not shown in FIG. 1 are concealed by these housings. In order to expose specific features, FIGS. 2A, 2B, 3, 4, and 5 provide illustrations with various housings, coverings, and/or components omitted. A person of skill in the art will appreciate that the omission of any component in any Figure is for the purpose of enhancing illustrative clarity of other components and in no way indicates the omitted component is somehow of lesser utility or value to the present systems, articles, and methods.

FIGS. 2A, 2B, 3, 4, and 5 provide further details of the inter- and intra-components of pod structures 101, 102, 103, 104, 105, 106, 107, and 108 from FIG. 1. For the purposes of the present systems, articles, and methods, pod structures 101, 102, 103, 104, 105, 106, 107, and 108 are substantially similar to one another; therefore, in order to reduce clutter, FIGS. 2A, 2B, 3, 4, and 5 illustrate further details of only one or two exemplary adjacent pod structures (e.g., pod structures 101 and 102 from FIG. 1). A person of skill in the art will appreciate that the details shown for two exemplary adjacent pod structures (e.g., pod structures 101 and 102 from FIG. 1) in FIGS. 2A, 2B, 3, 4, and 5 may similarly apply to any number of pod structures (e.g., including any or all of pod structures 103, 104, 105, 106, 107, and 108 from FIG. 1). The number of pod structures included in a wearable electronic device is dependent on at least the nature, function(s), and design of the wearable electronic device, and the present systems, articles, and methods may be applied to any wearable electronic device employing any number of pod structures.

Figure 2B:
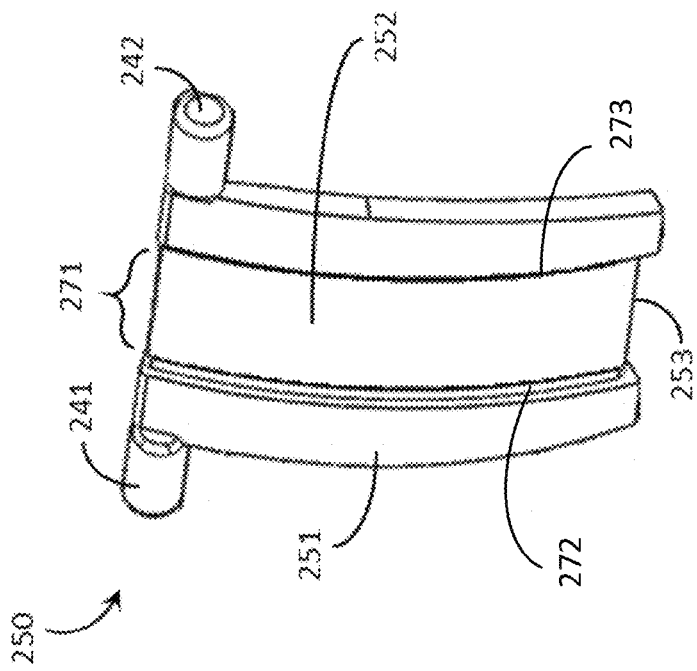
FIG. 2B is a perspective view of the strain mitigation system of the exemplary wearable electronic device from FIG. 2A with some components removed to reduce clutter.
Figure 2A:
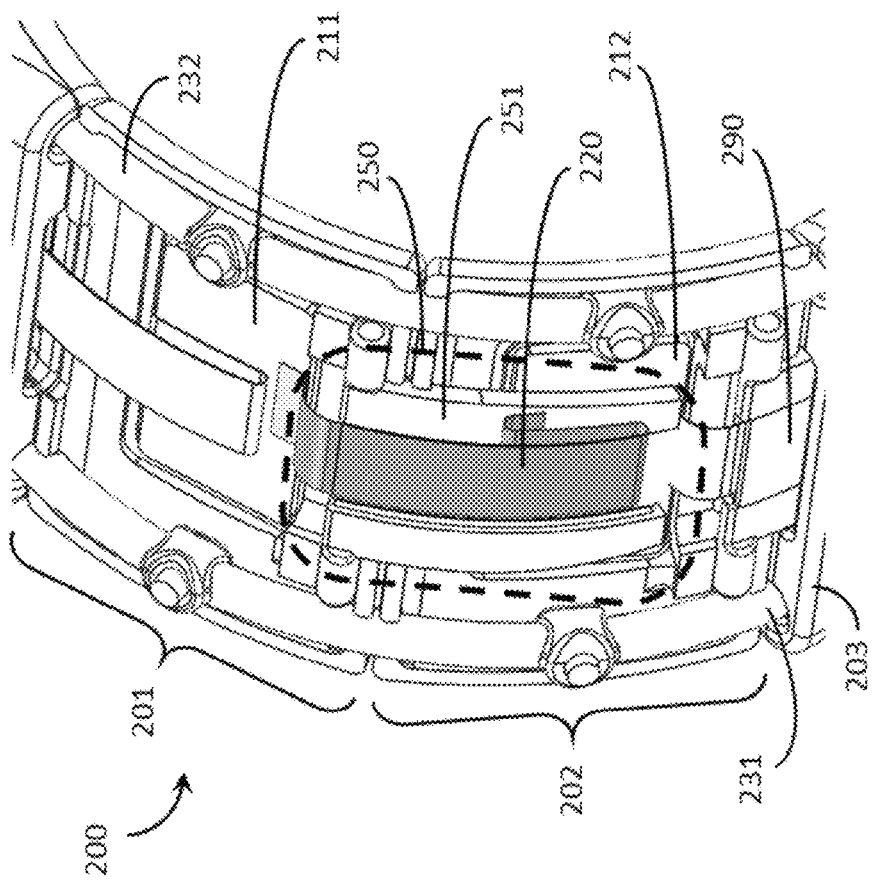
FIG. 2A is a perspective view of a portion of an exemplary wearable electronic device with a built-in strain mitigation system for mitigating physical strain on internal wiring in accordance with the present systems, articles and methods.

FIG. 2A is a perspective view of a portion of an exemplary wearable electronic device 200 with a built-in strain mitigation system 250 for mitigating physical strain on an internal wiring component 220 (shaded in FIG. 2A to enhance clarity) in accordance with the present systems, articles and methods. Device 200 is substantially similar to device 100 from FIG. 1. Specifically, device 200 includes two adjacent pod structures 201, 202 which are substantially similar to adjacent pod structures 101, 102 (respectively) from FIG. 1, except FIG. 2A does not depict housings covering pod structures 201, 202.

Device 200 includes two adaptive couplers 231, 232 that both provide adaptive physical coupling between pod structures 201 and 202. In exemplary device 200, adaptive couplers 231, 232 are each realized by a respective elastic band. Elastic band 231 is physically coupled to both pod structure 201 and pod structure 202 and provides elastic physical coupling therebetween, and elastic band 232 is also physically coupled to both pod structure 201 and pod structure 202 and also provides elastic physical coupling therebetween. A person of skill in the art will appreciate, however, that the adaptive coupling between pod structures 201 and 202 may be achieved by a variety of different adaptive couplers, including but not limited to: spring connectors; fabric, straps, or other flexible materials with length/tension adaptive by Velcro®, snaps, hooks, buttons, or other adjustable connectors; string, rope, or wire with length/tension adaptive by hand, dial, lever, or motor; etc. Furthermore, while device 200 employs two disconnected elastic bands 231, 232 to achieve adaptive physical coupling between pod structures 201, 202, adaptive physical coupling may similarly be achieved using more or fewer elastic bands.

Wiring component 220 is an example of an "electrically conductive pathway set" (as described previously in the context of FIG. 1) that provides electrical coupling between and/or through adjacent pod structures 201 and 202. In exemplary device 200, electrically conductive pathway set 220 is realized by a flexible printed circuit board that is electrically coupled to electrical circuitry 211 in pod structure 201 and to electrical circuitry 212 in pod structure 202 (details of electrical circuitry 211 and electrical circuitry 212 are omitted to reduce clutter). The flexible printed circuit board typically includes a number of electrically insulative layers (e.g., FR4, polyimide) and a number of electrically conductive paths or traces carried by one or more of the insulative layers. The electrically conductive paths or traces may be on an exterior surface of an outermost layer, or on an interior surface of either an outermost layer or an inner layer. The flexible printed circuit board may optionally include one or more vias electrically connecting electrically conductive paths or traces on two or more layers.

A person of skill in the art will appreciate that electrically conductive pathway set 220 may similarly be realized by other forms of electrically conductive pathways, including but not limited to: discrete wires, discrete cables, ribbon cables, elastic conductors, and the like. Similarly, electrical coupling between electrically conductive pathway set 220 and each of electrical circuitry 211, 212 may be achieved through a variety of different electrical connections, including but not limited to: one or multiple solder connections (e.g., hot bar solder connections), one or multiple connectors (e.g., ZIF connectors, plug and socket connectors, insulation-displacement connectors, crimp-on connectors), and the like.

As previously described, pod structures 201, 202 are advantageously flexibly coupled together by elastic bands 231, 232 in order to accommodate movements by the user (i.e., the "wearer") of wearable electronic device 200. Such movements can impose physical strains (e.g., stretches, torsions, twists, pulls, and so on) on flexible printed circuit board 220. In accordance with the present systems, articles and methods, strain mitigation system 250 mitigates physical strain on flexible printed circuit board 220. In exemplary device 200, strain mitigation system 250 comprises a guide structure 251 that is physically coupled to pod structure 201 and projects at least partially over electrical circuitry 212 in pod structure 202. Throughout this specification and the appended claims, the term "over" is used in a general sense without specific orientation and therefore includes "under," "across," and similar configurations. A first portion of flexible printed circuit board 220 extends across a length of guide structure 251 such that at least a portion of guide structure 251 serves as a bearing surface for flexible printed circuit board 220. Since flexible printed circuit board 220 may include multiple electrically conductive pathways, the configuration depicted in FIG. 2A ensures that at least a first portion of each electrically conductive pathway in flexible printed circuit board 220 extends across a length of guide structure 251. The entirety of flexible printed circuit board 220 is shaded in FIG. 2A (including portions of flexible printed circuit board 220 that are "behind" or otherwise visually obscured by other components of device 200 in the perspective view of FIG. 2A) in order to clearly illustrate the serpentine path taken by flexible printed circuit board 220 through strain mitigation system 250. To more clearly call out some of the features of strain mitigation system 250 and the relationships between guide structure 251 and flexible printed circuit board 220, FIG. 2B is provided.

FIG. 2B is a perspective view of a portion of strain mitigation system 250 of device 200 from FIG. 2A with the other components of device 200 removed. Some components of strain mitigation system 250 are not included in FIG. 2B to reduce clutter. FIG. 2B clarifies that guide structure 251 of strain mitigation system 250 includes a first surface 252 and an edge 253. Guide structure 251 also includes a second surface opposite first surface 252 and so not visible in FIG. 2B (i.e., a surface on the opposite side of guide structure 251 in relation to first surface 252). With reference to both FIG. 2A and FIG. 2B, a first portion of flexible printed circuit board 220 extends across a length of first surface 252 of guide structure 251, a second portion of flexible printed circuit board 220 bends around edge 253 of guide structure 251, and a third portion of flexible printed circuit board 220 extends across at least a portion of a length of the second surface (not visible in FIG. 2B) of guide structure 251. The path followed by flexible printed circuit board 220 over or through guide structure 251 is a serpentine path characterized by flexible printed circuit board 220 wrapping around guide structure 251 and/or turning back on itself at least once. In this configuration, the length of the third portion of flexible printed circuit board 220 that extends across at least a portion of a length of the second surface of guide structure 251 is variable and depends on the distance between adjacent pod structures 201 and 202. In FIG. 2A, adjacent pod structures 201 and 202 are depicted in close proximity to one another (e.g., touching one another) and elastic bands 231 and 232 are retracted; however, the physical coupling provided by elastic bands 231 and 232 is designed to be adaptive (i.e., extendable, extensible, flexible, stretchable, etc.) to accommodate the sizes and movements of different users. Elastic bands 231 and 232 may be extended and the distance between adjacent pod structures 201 and 202 may be increased. When the distance between adjacent pod structures 201 and 202 is increased, guide structure 251 slides over electrical circuitry 212 in pod structure 202 and the length of the third portion of flexible printed circuit board 220 that extends across at least a portion of a length of the second surface of guide structure 251 decreases. The length of the third portion of flexible printed circuit board 220 that extends across at least a portion of a length of the second surface of guide structure 251 is maximal when pod structures 201 and 202 are closest together (e.g., touching) and minimal when pod structures 201 and 202 are furthest apart. In this way, the physical coupling between pod structures 201 and 202 is made adaptive while mitigating the exposure of the electrical coupling (i.e., flexible printed circuit board 220) between pod structures 201 and 202 to varying tensions, stresses, torsions, strains, etc. Guide structure 251 also continues to shield flexible printed circuit board 220 from direct exposure to environmental elements and forces even when the distance between pod structures 201 and 202 is increased.

As depicted in FIG. 2B, guide structure 251 may include a recessed channel 271 that extends across a length thereof (e.g., across a length of first surface 252 of guide structure 251) for receiving flexible printed circuit board 220. In other words, flexible printed circuit board 220 may extend across a length of guide structure 251 within recessed channel 271 in first surface 252 of guide structure 251. Recessed channel 271 provides sidewalls 272, 273 that help to keep the first portion of flexible printed circuit board 220 in longitudinal and lateral position over the length of first surface 252 of guide structure 251. For example, at least first surface 252 and edge 253 provide bearing surfaces for flexible printed circuit board 220, while first surface 252 also provides a "longitudinal" guiding function of guide structure 251 and sidewalls 272, 273 provide a "transversal" or lateral guiding function of guide structure 251.

With reference to both FIG. 2A and FIG. 2B, strain mitigation system 250 may further include pivot structures 241 and 242 for pivotally (e.g., rotatably) coupling to pod structure 201. Thus, the physical coupling between guide structure 251 of strain mitigation system 250 and pod structure 201 may be pivotal coupling through pivot structures 241 and 242 of strain mitigation system 250. Pivotal coupling between guide structure 251 of strain mitigation system 250 and pod structure 201 may improve the fit of wearable device 200 for the user and/or facilitate mobility of the user. For example, as the distance between pod structures 201 and 202 is increased to accommodate the size and/or movements of a user (within the constraints imposed by the adaptive coupler(s), e.g., elastic bands 231 and 232), pivot structures 241 and 242 enable device 200 to better fit to the contours of the user's form and thereby further mitigate physical strains on flexible printed circuit board 220.

FIG. 2A shows only a portion of device 200 to emphasize features and details of a first strain mitigation system 250 between a first pod structure 201 and a second pod structure 202. However, as illustrated in FIG. 1, a wearable electronic device (e.g., device 100) may employ more than two pod structures (e.g., a third pod structure and/or at least one additional pod structure) and, accordingly, more than one strain mitigation system (e.g., a second strain mitigation system, a third strain mitigation system, and/or at least one additional strain mitigation system). For example, FIG. 2A depicts a portion of a third pod structure 203 adjacent pod structure 202 and a portion of a second strain mitigation system 290 pivotally coupled to pod structure 202 and projecting into pod structure 203.

As previously described, when the distance between adjacent pod structures 201 and 202 is increased, guide structure 251 slides over electrical circuitry 212 in pod structure 202 and the length of the third portion of flexible printed circuit board 220 that extends across at least a portion of a length of the second surface of guide structure 251 decreases. To facilitate the motion of guide structure 251 over electrical circuitry 212, strain mitigation system 250 may further include a structure or structures to provide slideable coupling between guide structure 251 and pod structure 202. An exemplary strain mitigation system that provides slideable coupling between guide structure 251 and pod structure 202 is illustrated in FIG. 3, FIG. 4, and FIG. 5.

Figure 3:
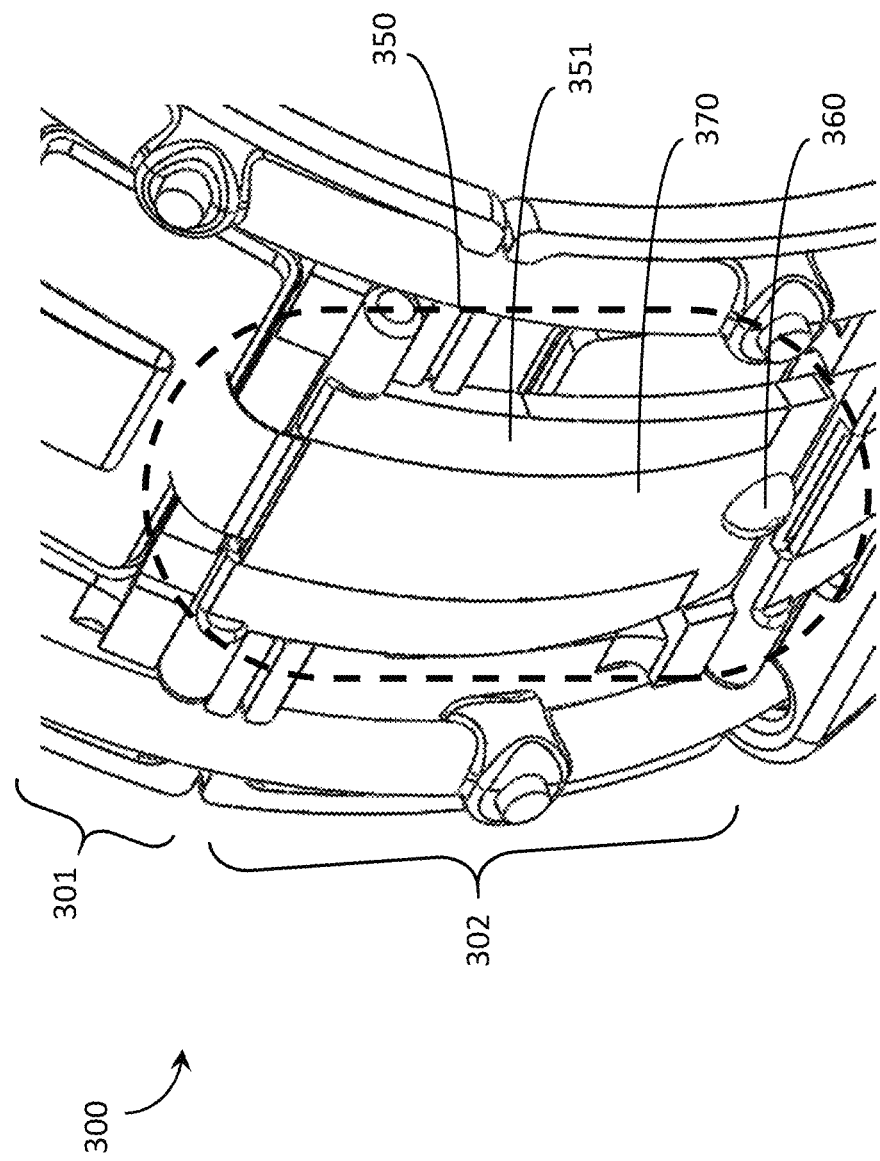
FIG. 3 is a perspective view of a portion of an exemplary wearable electronic device including two adjacent pod structures and a strain mitigation system, with one pod structure slideably coupled to the strain mitigation system in accordance with the present systems, articles and methods.

FIG. 3 is a perspective view of a portion of an exemplary wearable electronic device 300 including two adjacent pod structures 301 and 302 and a strain mitigation system 350, with pod structure 302 slideably coupled to strain mitigation system 350 (and pod structure 301 rotatably/pivotally coupled to strain mitigation system 350) in accordance with the present systems, articles, and methods. Device 300 is substantially similar to device 200 from FIG. 2A and strain mitigation system 350 is substantially similar to strain mitigation system 250 from both FIG. 2A and FIG. 2B; however, FIG. 3 clarifies that strain mitigation system further includes a protrusion 360 that protrudes out (i.e., away) from guide structure 351 in strain mitigation system 350. Protrusion 360 is depicted as protruding from a covering 370 that overlies at least apportion of the first surface (e.g., first surface 252) of guide structure 351; however, those of skill in the art will appreciate that protrusion 360 may alternatively be positioned anywhere on guide structure 351 and that strain mitigation system 350 may or may not include covering 370 in alternative designs. Protrusion 360 provides a component of the slideable coupling between guide structure 351 and pod structure 302 by mating with a receiving channel in a covering that overlies pod structure 302 (not shown in FIG. 3).

Figure 4:
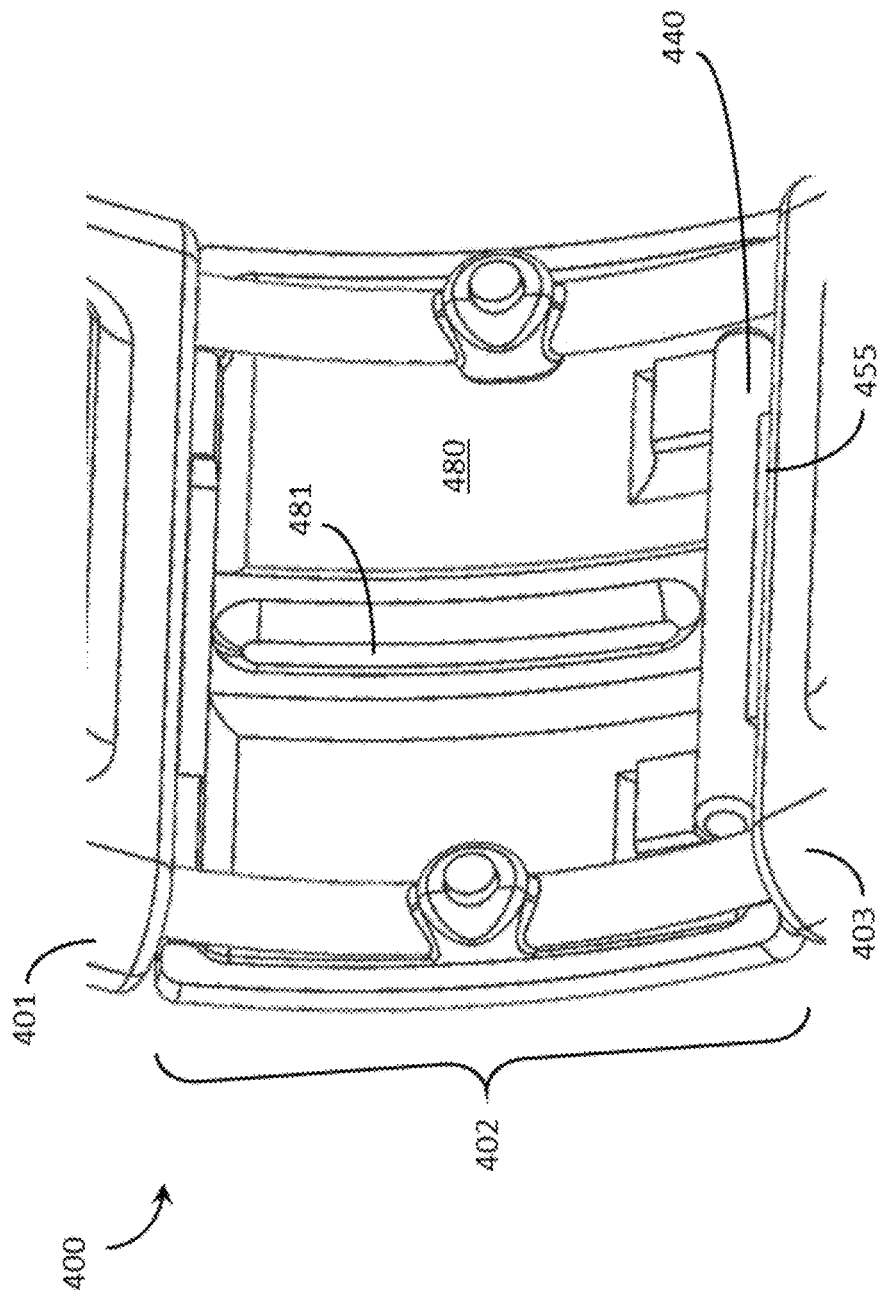
FIG. 4 is a perspective view of a portion of an exemplary wearable electronic device including a pod structure and showing a receiving channel in an underside of a covering that overlies the pod structure in accordance with the present systems, articles and methods.

FIG. 4 is a perspective view of a portion of an exemplary wearable electronic device 400 including a pod structure 402 (electrical circuitry is omitted from FIG. 4) and showing a receiving channel 481 in an underside of a covering 480 that overlies pod structure 402 in accordance with the present systems, articles and methods. Receiving channel 481 is sized and dimensioned to receive (e.g., mate with) a protrusion (e.g., protrusion 360 from FIG. 3, not shown in FIG. 4) from a guide structure (e.g., guide structure 351 from FIG. 3, not shown in FIG. 4) of a strain mitigation system (e.g., strain mitigation system 350 from FIG. 3; not shown in FIG. 4) and to thereby provide slideable coupling between the guide structure and pod structure 402. The slideable coupling between receiving channel 481 and the protrusion from the guide structure (e.g., protrusion 360 from guide structure 351) enables relative motion between pod structure 402 and an adjacent pod structure 401, but constrains this motion to directions substantially along the longitudinal axis of receiving channel 481. The longitudinal axis of receiving channel 481 may be substantially parallel to the longitudinal axis of an electrically conductive pathway set (e.g., flexible printed circuit board 220) and constraining motion to directions substantially parallel to the longitudinal axis of the electrically conductive pathway set advantageously mitigates physical strain on the electrically conductive pathway set, particularly when the electrically conductive pathway set is configured to be extendable/extensible in the longitudinal direction as in, for example, the serpentine configuration described for flexible printed circuit board 220 in FIG. 2A.

FIG. 4 depicts first pod structure 402 adjacent (i.e., in between) second pod structure 401 and third adjacent pod structure 403. An electrically conductive pathway set (not shown) provides electrical coupling between pod structure 402 and pod structure 403. Strain on the electrically conductive pathway set that electrically couples between pod structures 402 and 403 is mitigated by a strain mitigation system including a guide structure 455, a portion of which is visible in FIG. 4. Guide structure 455 is physically pivotally coupled to pod structure 402 by pivot structure 440. With reference to both FIG. 4 and FIG. 2B, a pivot structure may comprise a cylindrical rod 440 that is mated with (i.e., received in) at least one cylindrical housing (at 241, 242 in FIG. 2B) such that the cylindrical rod 440 may rotate within the cylindrical housing(s) at 241, 242. The cylindrical rod 440 may be fixedly physically coupled to the guide structure 455.

FIG. 5 is a perspective view of a portion of an exemplary wearable electronic device 500 including a pod structure 502 (electrical circuitry is omitted from FIG. 5) and a strain mitigation system 550 including a guide structure 551 slideably coupled to pod structure 502 in accordance with the present systems, articles, and methods. Pod structure 502 is overlain by a covering 580 that includes a receiving channel 581 (only a portion of which is visible in FIG. 5). Receiving channel 581 is substantially similar to receiving channel 481 depicted in FIG. 4. Strain mitigation system 550 includes a covering 570 that overlies a first surface (not visible in FIG. 5) of guide structure 551. Covering 570 includes a protrusion (similar to protrusion 360 from FIG. 3, not visible in FIG. 5) that protrudes towards covering 580 and into receiving channel 581 such that the slideable coupling between guide structure 551 and pod structure 502 is through the protrusion of covering 570 and the receiving channel 581 of covering 580. With reference back to the description of FIG. 2B, the view depicted in FIG. 5 also shows an edge 553 of guide structure 551 and a second surface 554 of guide structure 551.

FIGS. 3, 4, and 5 depict an exemplary configuration of slideable coupling between the guide structure of a strain mitigation system and a pod structure with the strain mitigation system including a protrusion projecting from the guide structure and the pod structure including a receiving channel formed in an underside of a covering. In accordance with the present systems, articles, and methods, similar slideable coupling may be achieved with a receiving channel formed in the guide structure of the strain mitigation system and a protrusion projecting from a covering in the pod structure. In general, one of the strain mitigation system and the pod structure may include a receiving channel and the other of the strain mitigation system and the pod structure may include a protrusion that protrudes into the receiving channel such that slideable coupling between the strain mitigation system and the pod structure is through the protrusion and the receiving channel.

The various embodiments described herein provide systems, articles, and methods for robust adaptive (e.g., flexible, stretchable, rotatable, etc.) electrical and physical coupling between components in wearable electronic devices. Such adaptability is advantageously provided in a wearable electronic device in order to accommodate different user sizes/forms and the movements of the user. Thus, adaptability is desirable from an ergonomic point-of-view. Physical strain on electrical coupling between elements of a wearable electronic device resulting from an adaptive physical coupler is mitigated through a strain mitigation system. Various components of the wearable electronic device may be adaptive, flexible, elastic, etc., to support ergonomic functionality and various components of the wearable electronic device may be rigid to support reliable electronic functionality. For example, any or all pod structures (e.g., pod structures 101, 102, 201, 202, 301, 302, 401, 402, 502, etc.) may be formed of substantially rigid material (e.g., plastic) to protect and provide a stable environment for the electrical circuitry therein. For example, any or all pod structures may include a (respective) housing having an inner volume, and any or all guide structures may project at least partially into the inner volume of a pod structure. Throughout this specification and the appended claims, the term "rigid" as in, for example, "substantially rigid material," is used to describe a material that has an inherent tendency to maintain its shape and resist malformation/deformation under the moderate stresses and strains typically encountered by a wearable electronic device.

In accordance with the present systems, articles and methods, a configuration of substantially rigid pod structures adaptively coupled together affords a further benefit. In the exemplary application of a wearable electromyography device described previously (i.e., in the context of FIG. 1), a configuration of substantially rigid pod structures adaptively coupled together provides substantially equal angular spacing between pod structures regardless of whether the adaptive physical coupling(s) therebetween is fully retracted, fully extended, or anywhere in between. Such provides substantially similar electromyography sensing performance regardless of the size of the user's wrist/arm/leg, etc., as described in U.S. Non-Provisional patent application Ser. No. 14/276,575, which is incorporated herein by reference in its entirety.

The various embodiments described herein may employ elastic conductors. For example, any or all pod structures, electrical circuitry, electrically conductive pathway sets, etc. may employ elastic conductors to enhance adaptability and better accommodate the size, form, and/or movements of a user.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other portable and/or wearable electronic devices, not necessarily the exemplary wearable electronic devices generally described above.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to: U.S. Provisional Patent Application Ser. No. 61/857,105; U.S. Provisional Patent Application Ser. No. 61/752,226 (now U.S. Non-Provisional patent application Ser. No. 14/155,107); U.S. Provisional Patent Application Ser. No. 61/768,322 (now U.S. Non-Provisional patent application Ser. No. 14/186,889); U.S. Provisional Patent Application Ser. No. 61/771,500 (now U.S. Non-Provisional patent application Ser. No. 14/194,252); and U.S. Non-Provisional patent application Ser. No. 14/276,575, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A wearable electronic device comprising:
a first pod structure that includes electrical circuitry;
a second pod structure that includes electrical circuitry;
a first adaptive coupler that provides adaptive physical coupling between the first pod structure and the second pod structure;
a first set of electrically conductive pathways to in use provide electrical coupling between the electrical circuitry of the first pod structure and the electrical circuitry of the second pod structure; and
a first strain mitigation system to in use mitigate strain on the first set of electrically conductive pathways, the first strain mitigation system comprising a first guide structure that is physically coupled to the first pod structure and projects at least partially over the electrical circuitry of the second pod structure, wherein a respective first portion of each electrically conductive pathway in the first set of electrically conductive pathways extends across a length of the first guide structure wherein the first set of electrically conductive pathways includes a first flexible printed circuit board; and
wherein the first guide structure includes a first surface, an edge, and a second surface opposite the first surface, and wherein a first portion of the first flexible printed circuit board extends across a length of the first surface of the first guide structure, a second portion of the first flexible printed circuit board bends around the edge of the first guide structure, and a third portion of the first flexible printed circuit board extends across at least a portion of a length of the second surface of the first guide structure.

2. The wearable electronic device of claim 1 wherein the first adaptive coupler includes an elastic material that is physically coupled to both the first pod structure and the second pod structure to, in use, provide elastic physical coupling between the first pod structure and the second pod structure.

3. The wearable electronic device of claim 1 wherein the first strain mitigation system further includes at least one pivot structure, and wherein the first guide structure is pivotally coupled to the first pod structure through the at least one pivot structure.

4. The wearable electronic device of claim 1 wherein the first guide structure includes a recessed channel that extends across a length of the first guide structure, and wherein the first flexible printed circuit board extends across a length of the first guide structure within the recessed channel in the first guide structure.

5. The wearable electronic device of claim 1 wherein the first strain mitigation system is slideably coupled to the second pod structure.

6. The wearable electronic device of claim 5 wherein one of the first strain mitigation system and the second pod structure includes a receiving channel and the other of the first strain mitigation system and the second pod structure includes a protrusion that protrudes into the receiving channel, and wherein slideable coupling between the first strain mitigation system and the second pod structure is through the protrusion and the receiving channel.

7. The wearable electronic device of claim 1 wherein the first pod structure and the second pod structure are each formed of substantially rigid material.

8. The wearable electronic device of claim 1 wherein the second pod structure includes a housing having an inner volume, and wherein the first guide structure projects at least partially into the inner volume of the housing of the second pod structure.

9. The wearable electronic device of claim 1 wherein the second pod structure is positioned adjacent the first pod structure, and further comprising:
   a third pod structure that includes electrical circuitry, the third pod structure positioned adjacent the second pod structure;
   an adaptive physical coupling between the second pod structure and the third pod structure;
   a second set of electrically conductive pathways to in use provide electrical coupling between the electrical circuitry of the second pod structure and the electrical circuitry of the third pod structure; and
   a second strain mitigation system to in use mitigate strain on the second set of electrically conductive pathways, the second strain mitigation system comprising a second guide structure that is physically coupled to the second pod structure and projects at least partially over the electrical circuitry of the third pod structure, wherein a respective first portion of each electrically conductive pathway in the second set of electrically conductive pathways extends across a length of the second guide structure.

10. The wearable electronic device of claim 9 wherein the adaptive physical coupling between the second pod structure and the third pod structure is through the first adaptive coupler.

11. The wearable electronic device of claim 9, further comprising:
   a second adaptive coupler that provides the adaptive physical coupling between the second pod structure and the third pod structure.

12. The wearable electronic device of claim 9, further comprising:
   an adaptive physical coupling between the third pod structure and the first pod structure.

13. The wearable electronic device of claim 9, further comprising:
   at least one additional pod structure that includes electrical circuitry, each additional pod structure positioned adjacent at least one other pod structure;
   a respective adaptive physical coupling between each additional pod structure and an adjacent at least one other pod structure;
   a respective additional set of electrically conductive pathways corresponding to each additional pod structure, wherein each additional set of electrically conductive pathways in use provides electrical coupling between the electrical circuitry of a corresponding additional pod structure and the electrical circuitry of the adjacent at least one other pod structure; and
   a respective additional strain mitigation system corresponding to each additional set of electrically conductive pathways, each additional strain mitigation system to in use mitigate strain on a corresponding additional set of electrically conductive pathways, wherein each additional strain mitigation system comprises a respective corresponding guide structure that is physically coupled to the adjacent at least one other pod structure and projects at least partially over the electrical circuitry of the corresponding additional pod structure, and wherein a respective first portion of each electrically conductive pathway in the corresponding additional set of electrically conductive pathways extends across a length of the respective corresponding guide structure.

14. The wearable electronic device of claim 13 wherein the first pod structure, the second pod structure, the third pod structure, and the at least one additional pod structure are collectively arranged in an annular configuration with each respective pod structure positioned adjacent two other pod structures.

15. The wearable electronic device of claim 1 wherein at least one of the first pod structure and the second pod structure includes an electromyography sensor.

16. A wearable electronic device comprising:
   a set of pod structures arranged in an annular configuration with each pod structure in the set of pod structures positioned adjacent two other pod structures in the set of pod structures, wherein each pod structure includes respective electrical circuitry;
   an adaptive coupler that physically couples each pod structure in the set of pod structures to two adjacent pod structures in the set of pod structures, wherein the adaptive coupler physically binds the set of pod structures in the annular configuration;
   a plurality of electrically conductive pathway sets, wherein each respective pair of adjacent pod structures in the set of pod structures is electrically coupled together by a respective electrically conductive pathway set in the plurality of electrically conductive pathway sets; and
   a set of strain mitigation systems, each to in use mitigate strain on a respective electrically conductive pathway set in the plurality of electrically conductive pathway sets, wherein each strain mitigation system includes a respective guide structure that is physically coupled to a respective pod structure in the set of pod structures and that projects at least partially over or within an adjacent pod structure in the set of pod structures, and wherein each electrically conductive pathway set in the plurality of electrically conductive pathway sets extends across a length of the guide structure of a respective strain mitigation system in the set of strain mitigation systems wherein each electrically conductive pathway set in the plurality of electrically conductive pathway sets comprises a respective flexible printed circuit board; and
   wherein each respective guide structure includes a respective first surface, a respective edge, and a respective second surface opposite the respective first surface, and for each flexible printed circuit board:

a first portion of the flexible printed circuit board extends across a length of the first surface of a corresponding guide structure, a second portion of the flexible printed circuit board bends around the edge of the corresponding guide structure, and a third portion of the flexible printed circuit board extends across at least a portion of a length of the second surface of the corresponding guide structure.

17. The wearable electronic device of claim 16 wherein the adaptive coupler includes elastic material.

18. The wearable electronic device of claim 17 wherein the adaptive coupler includes at least two disconnected pieces of elastic material.

19. The wearable electronic device of claim 17 wherein the adaptive coupler consists of a single piece of elastic material.

20. The wearable electronic device of claim 16 wherein each strain mitigation system in the set of strain mitigation systems includes at least one respective pivot structure, and wherein the respective guide structure of each strain mitigation system in the set of strain mitigation systems is pivotally coupled to a respective pod structure through the at least one respective pivot structure.

21. The wearable electronic device of claim 16 wherein the first surface of each guide structure includes a respective recessed channel, and for each flexible printed circuit board:
the first portion of the flexible printed circuit board extends across the length of the first surface of the corresponding guide structure within the recessed channel in the first surface of the corresponding guide structure.

22. The wearable electronic device of claim 16 wherein each strain mitigation system includes a respective slideable coupling between the respective guide structure and the adjacent pod structure in the set of pod structures over or within which the respective guide structure projects.

23. The wearable electronic device of claim 16 wherein each pod structure in the set of pod structures is formed of substantially rigid material.

24. The wearable electronic device of claim 16 wherein each pod structure in the set of pod structures includes a respective housing having a respective inner volume, and wherein each respective guide structure projects at least partially into the inner volume of the respective housing of a respective adjacent pod structure in the set of pod structures.

25. The wearable electronic device of claim 16 wherein at least one pod structure in the set of pod structures includes an electromyography sensor.

* * * * *